United States Patent [19]
Bello et al.

[11] Patent Number: 5,716,621
[45] Date of Patent: Feb. 10, 1998

[54] NONOCCLUSIVE DRUG DELIVERY DEVICE AND PROCESS FOR ITS MANUFACTURE

[75] Inventors: Gastone P. Bello, Monmouth Beach; John W. Lyle, Belmar; Donald A. Johnson, Toms River, all of N.J.

[73] Assignee: PharmaDyn, Inc., Farmingdale, N.J.

[21] Appl. No.: 675,348

[22] Filed: Jul. 3, 1996

[51] Int. Cl.⁶ .................. A61K 9/70; A61F 13/20
[52] U.S. Cl. ............ 424/443; 424/449; 604/366; 604/369; 604/370; 604/375
[58] Field of Search ................ 424/449, 443; 604/366, 369, 370, 375

[56] References Cited

U.S. PATENT DOCUMENTS

| | | | |
|---|---|---|---|
| 2,858,830 | 11/1958 | Robins | 128/156 |
| 3,025,854 | 3/1962 | Scholl | 128/156 |
| 3,062,210 | 11/1962 | Scholl | 128/156 |
| 3,113,568 | 12/1963 | Robins | 128/156 |
| 3,156,242 | 11/1964 | Crowe, Jr. | 128/296 |
| 3,157,178 | 11/1964 | Bentov | 128/156 |
| 3,665,918 | 5/1972 | Lindquist et al. | 128/156 |
| 3,849,238 | 11/1974 | Gould et al. | 161/159 |
| 3,900,027 | 8/1975 | Keedwell | 128/268 |
| 3,949,742 | 4/1976 | Nowakowski | 128/155 |
| 3,975,567 | 8/1976 | Lock | 428/315 |
| 3,978,855 | 9/1976 | McRae et al. | 128/156 |
| 4,233,969 | 11/1980 | Lock et al. | 128/90 |
| 4,450,833 | 5/1984 | Brooks et al. | 128/90 |
| 4,530,353 | 7/1985 | Lauritzen | 128/156 |
| 4,538,603 | 9/1985 | Pawelchak et al. | 128/156 |
| 4,561,435 | 12/1985 | McKnight et al. | 128/156 |
| 4,625,720 | 12/1986 | Lock | 128/156 |
| 4,655,210 | 4/1987 | Edenbaum et al. | 428/315 |
| 4,733,659 | 3/1988 | Edenbaum et al. | 128/156 |
| 4,753,231 | 6/1988 | Lang et al. | 128/156 |
| 4,773,408 | 9/1988 | Cilento et al. | 128/156 |
| 4,773,409 | 9/1988 | Cilento et al. | 128/156 |
| 4,810,582 | 3/1989 | Gould et al. | 428/423.1 |
| 4,906,240 | 3/1990 | Reed et al. | 604/307 |
| 4,933,184 | 6/1990 | Tsuk | 424/449 |
| 4,960,594 | 10/1990 | Honeycutt | 424/445 |
| 4,977,892 | 12/1990 | Ewall | 128/156 |
| 5,098,500 | 3/1992 | Reed et al. | 156/253 |
| 5,246,705 | 9/1993 | Vankatraman et al. | 424/448 |
| 5,292,777 | 3/1994 | DesMarais et al. | 521/64 |
| 5,322,695 | 6/1994 | Shah et al. | 424/448 |
| 5,352,711 | 10/1994 | DesMarais | 521/149 |
| 5,393,528 | 2/1995 | Staab | 424/436 |
| 5,409,472 | 4/1995 | Rawlings et al. | 604/307 |

*Primary Examiner*—Thurman K. Page
*Assistant Examiner*—Kathryne E. Shelborne
*Attorney, Agent, or Firm*—Dilworth & Barrese

[57] ABSTRACT

A nonocclusive drug delivery device includes (a) an open cell, flexible, oleophilic thermoplastic resin foam layer, (b) a substantially moisture vapor permeable, liquid impermeable, flexible thermoplastic barrier layer bonded to the upper surface of the foam layer, (c) a pressure sensitive adhesive layer and (d) a drug composition comprising a drug and an oleophilic drug delivery vehicle.

4 Claims, 4 Drawing Sheets

5,716,621

NONOCCLUSIVE DRUG DELIVERY DEVICE AND PROCESS FOR ITS MANUFACTURE

BACKGROUND OF THE INVENTION

This invention relates to a nonocclusive drug delivery device and to a method for its manufacture.

One known type of transdermal drug delivery device, also variously referred to as a medical bandage, treatment pad, drug patch, etc., includes a drug depot, or reservoir, in the form of a drug-storing matrix or carrier and an adhesive for attaching or securing the device to a surface of unbroken skin.

In one particular type of construction, a known drug delivery device is provided as a laminate of a thermoplastic microcellular foam layer carrying a measured quantity of drug or drug-containing composition, the upper surface of the foam layer being bonded to a thermoplastic fill barrier layer and its lower surface possessing a contact adhesive. It has been found that a drug delivery device of this general construction may be liable to one or more drawbacks which preclude its effective use and practical acceptance. For example, unless the peel strength of the device is significantly less than the strength of the bond between the foam and barrier layers, on peeling the device from the skin, separation (i..e, delamination) of the foam and barrier layers may occur with portions of foam continuing to adhere to the skin. Another problem can arise when, due to the physico-chemical nature of the foam and the drug or drug-containing composition, the latter migrates into the adhesive thereby impairing the strength of the bond by which the device is held to the skin.

SUMMARY OF THE INVENTION

In accordance with the present invention, a nonocclusive drug delivery device is provided which comprises:

a) an open cell, flexible, oleophilic thermoplastic resin foam layer possessing upper and lower surfaces and predetermined adhesive, drug depot and drug migration barrier zones;

b) a substantially moisture vapor permeable, liquid impermeable, flexible thermoplastic barrier layer bonded to the upper surface of the foam layer, the composite of the barrier and foam layers possessing a moisture vapor transmission rate of at least about 500 g/m$^2$/24 h at 100% r.h and 32° C., the bond strength between the barrier layer and the foam layer being such as to resist separation of the barrier layer from the foam layer when the drug delivery device is subjected to the flexing and/or stretching forces normally encountered during its useful applied life;

c) a pressure sensitive adhesive within the adhesive zone of the foam layer, the adhesive layer imparting a peel strength to the drug delivery device which is sufficiently below that of the bond strength between the foam layer and the barrier layer such that upon peeling the device from the skin, substantially all of the foam layer remains bonded to the barrier layer; and, d) a drug composition comprising a therapeutically effective amount of at least one drug in an oleophilic drug delivery vehicle, the drug composition being contained within the drug depot zone of the foam layer and separated from the adhesive zone by the barrier zone.

The foregoing drug delivery device effectively overcomes each of the above-noted drawbacks associated with the prior art drug delivery device. Thus, the device of this invention resists delamination when pulled from the skin and since its drug-containing component remains isolated from the adhesive component by a barrier zone, there is little, if any, likelihood of the drug composition reaching the adhesive and impairing its effectiveness.

DESCRIPTION OF THE PREFERRED EMBODIMENTS

Figure 1:
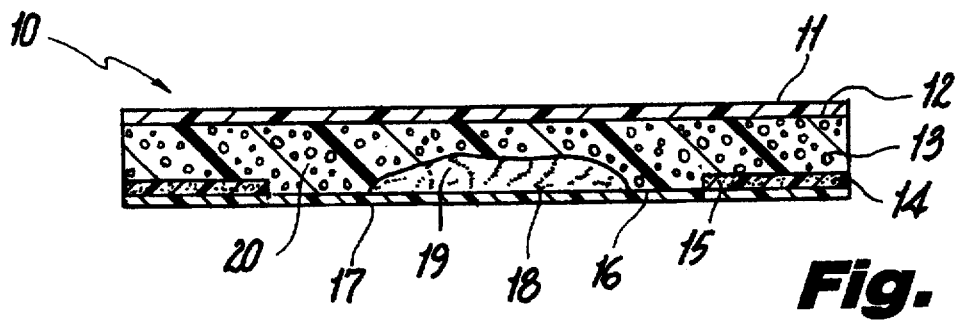
FIG. 1 is a cross-sectional view of one embodiment of a drug delivery device in accordance with the invention.

One embodiment of a nonocclusive drug delivery device in accordance with this invention is shown generally in FIG. 1 at 10. The drug delivery device includes a substantially moisture vapor permeable, liquid impermeable, flexible thermoplastic barrier layer 11 bonded to, and generally coextensive with, upper surface 12 of open cell, flexible, oleophilic thermoplastic resin foam layer 13. Pressure sensitive adhesive 14 occupies a zone, or stratum, 15 on lower surface 16 of foam layer 13 for securing the drug delivery device to the skin. Drug composition 18 occupies drug depot zone 19 and is separated from adhesive zone 15 by barrier zone 20 which prevents or inhibits migration of the drug composition into adhesive 14. A release liner 17 seals and protects lower surface 16 of the foam layer during the residency of drug delivery device 10 within its package.

The minimum strength of the bond between barrier layer 11 and foam layer 13 is one of several critical requirements of the drug delivery device of this invention and must be sufficient to prevent or inhibit separation, i.e., delamination, of the barrier layer from the foam layer under the sort of flexing and/or stretching forces that may be encountered during the useful life of the applied device. In general, bond strengths of at least about 2 newtons (N), preferably at least about 3 N and more preferably at least about 5 N will generally provide satisfactory results in this regard. However the bond between layers 11 and 13 may be achieved, it is necessary that the bond itself not result in a significant reduction in the moisture vapor transmission rate (MVTR) of the assembled layers. While known and conventional contact adhesives can readily provide barrier layer-to-foam layer bond strengths of 2 N and greater, they may be disadvantageous in reducing the MVTR of the assembled layers to an unacceptable degree. Accordingly, it is preferred herein to employ a nonadhesive bonding technique, e.g., one employing heat such as flame bonding that is capable of producing the desired bond strengths but without significantly reducing the MVTR of the composite formed from layers 11 and 13.

In general, the MVTR of the barrier layer-foam layer subassembly will be at least about 500, preferably at least about 1000 and more preferably at least about 1200, g/m$^2$/24 h at 100% r.h. and 32° C. as measured by ASTM F1249-90.

Another critical requirement of the drug delivery device of this invention is that whatever the bond strength between barrier layer 11 and foam layer 13, the contact adhesive must impart a peel strength to the drug delivery device, i.e., the amount of force required to peel the spent drug delivery device from the skin, which is less, preferably at least about 20 percent less and more preferably at least about 40 percent less, than such bond strength in order to prevent or minimize the separation of the barrier layer from the foam layer when the spent drug delivery device is peeled from the skin.

Barrier layer 11 can be any thermoplastic film possessing an MVTR of one of the aforestated values. Preferably, the barrier layer can be a polyurethane film possessing an average thickness of from about 0.5 to about 3.5 mils and preferably from about 1.0 to about 1.5 mils and a tensile strength of at least about 2500 psi and preferably at least about 3500 psi.

Foam layer 13 in its as-manufactured state is an open cell, flexible, oleophilic foam that provides a stable matrix for the drug and its oleophilic delivery vehicle. By "stable matrix" is meant that property of the foam which, owing to its oleophilic character, enables the foam to function not only as a depot, or reservoir, for the oleophilic drug composition, but confines the composition to zone 19 which is separated by barrier zone 20 from zone 15 occupied by pressure sensitive adhesive 14. Thus, the oleophilic characteristics of the foam layer prevent or inhibit migration of the drug composition into adhesive zone 15 where it could destroy or impair the effectiveness of adhesive 14 in securing the drug delivery device to the skin. Another advantageous characteristic of the drug delivery device herein is its ability to maintain continuous contact between the drug composition and the skin thus assuring that the drug will be constantly available at the site of its administration.

In general, the useful foams possess a density of from about 0.8 to about 8.0 and preferably from about 1.2 to about 4.8 lb/ft, a number of pores per inch of from about 30 to about 120 and preferably from about 60 to about 90, and can be fully or partially reticulated or nonreticulated. The average thickness of the foam layer can vary from about 30 to about 100 mils and for many applications is preferably from about 40 to about 70 mils. Suitable foams that can be employed herein include the untreated oleophilic (i.e., hydrophobic) open cell polyurethane foams disclosed in U.S. Pat. No. 5,352,711, the contents of which are incorporated by reference herein.

Pressure sensitive adhesive 14 can be selected from any of the known and conventional medical grade adhesives, e.g., those based on polyacrylic, polyvinylether, or polyurethane resins. It is an essential requirement that the amount of adhesive 14 applied to zone 15 of foam layer 13 be sufficient to achieve an acceptable level of adhesion of drug delivery device 10 to the skin but, as previously stated, with a resulting peel strength that is sufficiently below the bond strength between the barrier and foam layers. The amount of adhesive that will satisfy these criteria can be readily determined by simple and routine testing. Ordinarily, a medical grade polyacrylic adhesive such as Durotak® (National Starch & Chemical Company, Bridgewater, N.J.) or Gelva® (Monsanto Inc., St. Louis, Mo.) applied to a thickness of from about 1 to about 3.5 mils and preferably from about 2.0 to about 2.5 mils (depending, of course, on the thickness of the foam layer), or applied at a rate of from about 25 to about 100 g/cm$^2$ and preferably from about 50 to about 65 g/cm$^2$, will meet these requirements reasonably well.

A process for manufacturing the drug delivery device of this invention is schematically illustrated in FIGS. 2A–E.

Figure 2A:
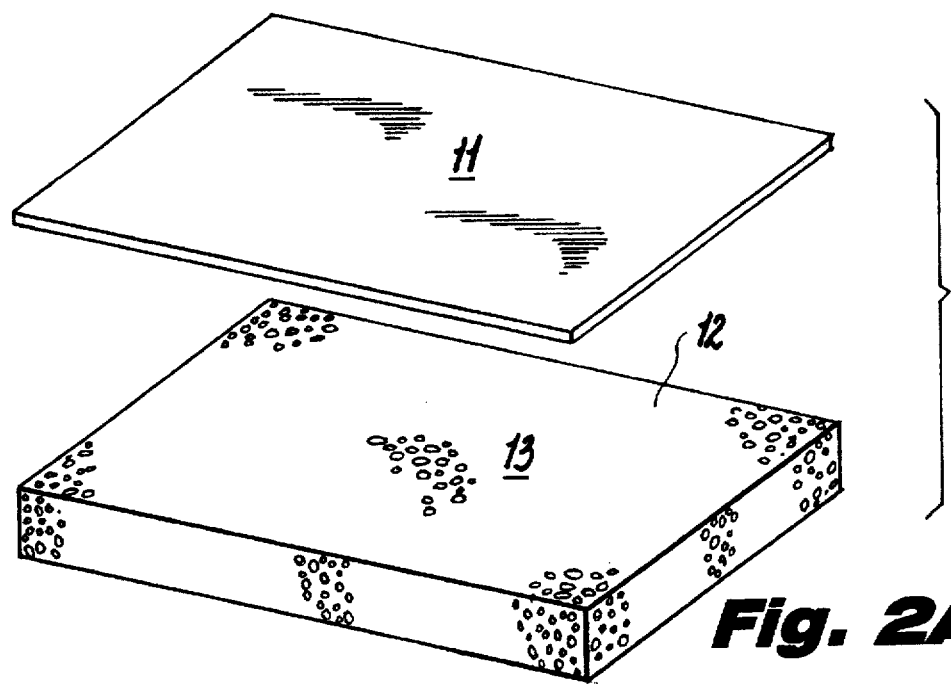
FIGS. 2A–E schematically illustrate the principal stages in the manufacture of the drug delivery device of FIG. 1.

As shown in FIG. 2A, barrier layer 11 is bonded to upper surface 12 of foam layer 13 employing a suitable bonding technique, preferably, a flame bonding procedure for the reason stated above. Flame bonding, or flame lamination, the details of which are well known, involves the superficial softening or melting of upper surface 12 of foam layer 13 and while surface 12 is in this state, the application of barrier layer 11 thereto. Conditions of the flame bonding operation include the temperature of the flame, the proximity of surface 12 of the foam to the flame and the duration of exposure of this surface to the flame. The conditions that are employed for a particular flame bonding operation will depend on the properties of the foam and barrier layers, the bond strength desired and similar factors of which those skilled in the art are aware. For the preferred polyurethane barrier film and polyurethane foam components, a flame temperature of from about 1800° to about 2200° C., a distance from the flame to the upper surface of the foam of up to about 3 cm and an exposure time of such surface of from about 25 to about 40 milliseconds will usually provide the desired minimum bond strengths or better.

In another type of nonadhesive bonding procedure, vacuum lamination, a vacuum is applied to the lower surface of the foam layer and a molten thermoplastic layer intended to provide the barrier layer is cast upon the upper surface of the foam layer. The vacuum partially draws the cast layer of molten resin into the structure of the foam so that when the resin cools and solidifies, it provides the barrier layer securely bonded to the foam layer.

Figure 2B:
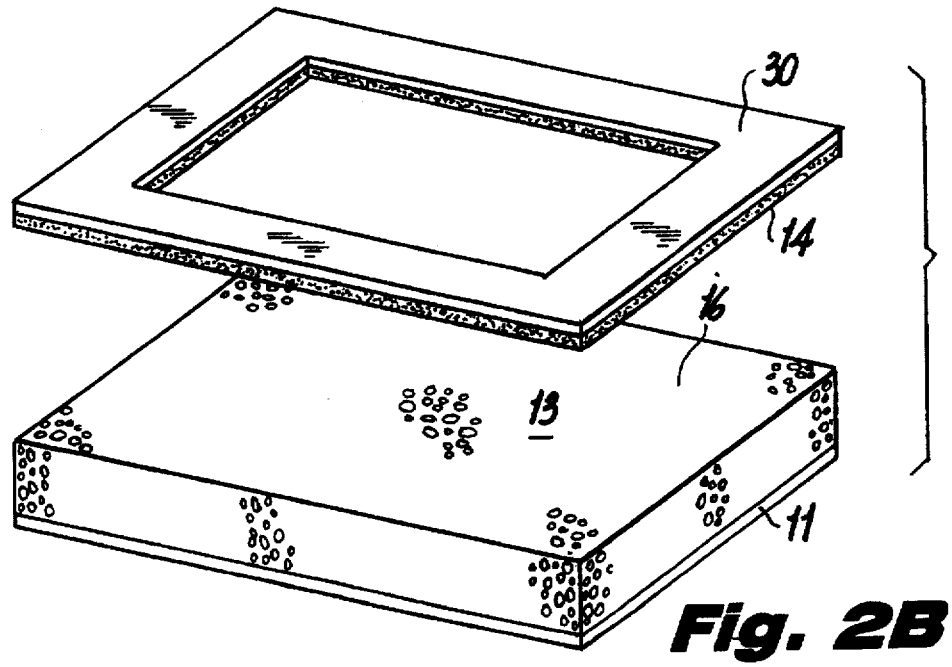
Figure 2C:
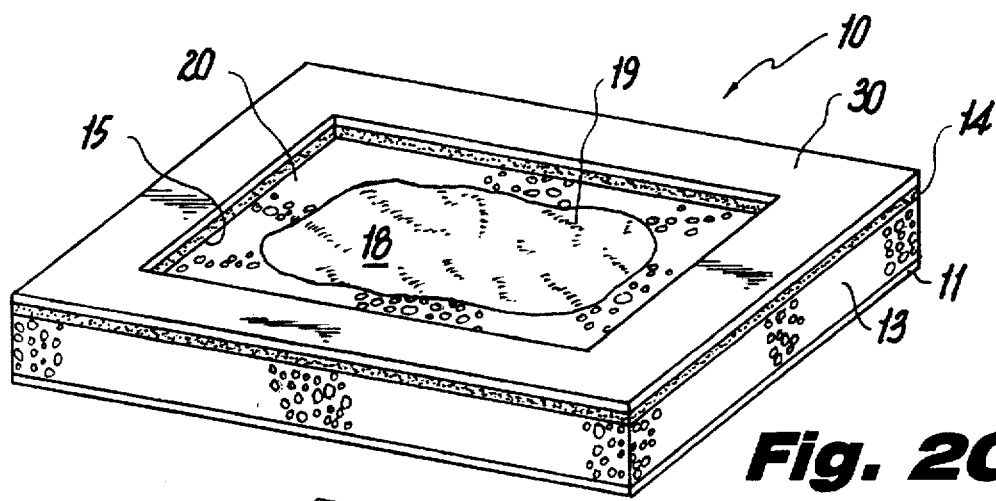

In FIG. 2B, the barrier layer/foam layer composite has been inverted (its orientation for this and the remaining operations shown) and a first, or temporary, release liner 30 with medical grade adhesive 14 applied thereto is brought into contact with zone 15 of lower surface 16 of foam layer 13. As shown in FIG. 2C, release liner 30 possesses cut-out portion 22 providing an opening, or "window", through which drug composition 18 is applied to exposed drug depot zone 19 of foam layer 13. Drug composition 18 is applied in a fluid or semi-fluid state which, e.g., can be achieved, by heating, so that the composition spreads out somewhat from its initial point of application to zone 19. However, after reaching the maximum extent of its spread and hardening, drug composition 18 will be surrounded by barrier zone 20 lying between it and zone 15 through which contact adhesive 14 has infiltrated.

A large variety of drug-containing compositions can be incorporated into the drug depot zone of foam layer 13 of drug delivery device 10. The term "drug" is used herein in its broadest sense as referring to any substance or composition possessing therapeutically or medicinally beneficial activity and includes prescription and nonprescription pharmaceuticals, medicinals, medicaments, active ingredients of cosmetic and personal care preparations, and the like. Specific drugs that can be incorporated into drug composition 18 include topically delivered local anesthetics such as benzocaine, procaine hydrochloride, tetracaine, tetracaine hydrochloride, dibucaine, lidocaine, lidocaine hydrochloride, bupivicaine, dyclonin, etidocaine, mepivicaine, butamen picrate, dimethisoquin hydrochloride, cyclomethylcaine sulfate, and the like; analgesics and anti-inflammatory agents such as buprenorphin, butophanol tartrate, acetaminophen, fentanyl, mefenamic acid, flutenamic acid, diclofenac, oxyphenbutazone, phenybutazone, ibuprofen, flurbiprofen, naproxen, menthol, methyl salicylate, phenol, salicylic acid, benzyl alcohol, camphor, camphorated metacresol, juniper tar, resorcinol, allyl isothiocyanate, capsaicin, and the like; corticosteroids such as alclometasone dipropionate, amcinocide, hydrocortisone, betamethasone dipropionate, betamethasone valerate, desoximetasone, clobetasol propionate, flurandrenolide, halcinonide, halobetasol, estradiol, testosterone, progesterone, fluticasone, clobetasol, dexamethasone, dexonide, fluocinolone acetonide, flucinonide, medroxyprogesterone, mometasone furoate, triamcinolone, and the like; antibiotics such as bacitracin, bacitracin zinc, chlortetracycline hydrochloride, chlorhexadine gluconate, clindamycin, cliquinol, neomycin sulfate, polymyxin B sulfate, erythromycin, gentamicin, sulfathiazole, sulfacetamide, sulfabenzamide, oxytetracycline hydrochloride, tetracycline, and the like; antimicrobial agents such as benzalkonium chloride, chlorhexidine gluconate, hexaclorophene, mafenide acetate, nitrofurazone, nystatin, acetosulfamine, clortrimazole, povidone-iodine, and the like; antifungal agents such as amphotericin B, butoconazole, cetylpyridinium chloride, chlorxylenol, cyclopirox olamine, clioquinol, clotrimazole, sulconazole nitrate, nystatin, oxyconazole, econazole nitrate, ketoconazole, miconazole nitrate, naftifine hydrochloride, pentamycin, pyrrolinitrin, terbinafine, triacetin, and the like; debriding agents such as deoxyribonuclease, collagenolytic, debridement, fibrinolytic or proteolytic enzymes, papain, papain-urea, and the like; antihistamines such as chlorcyclizine hydrochloride, diphenylhydramine hydrochloride, tripelennamine hydrochloride, and the like; antiepileptics such as nitrazepam, meprobamate, clonazepam, and the like; coronary vasodilators such as nitroglycerine, dipyridamole, erythritol, tetranitrate, pentaerythritol tetranitrate, propatylnitrate, and the like; dermatologicals such as retinal, retinol, retinoic acid and their derivatives, hydroxyacids, alphaketoacids, and the like; and other drugs such as benzoyl peroxide, podofilox, masoprocol, nicotine, scopolamine, nitroglycerine, fluorouracil, hydrocolloids, hydroquinone, monobenzone, tretinoin and acyclovir.

These and other drugs are provided in some suitable diffusable oleophilic medium, e.g., an ointment, paste or other oleophilic vehicle, in accordance with known established pharmaceutical formulating practice. In those cases where rapid penetration of the drug is desired, it may be advantageous to include one or more penetration enhancers in the diffusable drug composition. Included among the penetration enhancers that can be used herein are butylene glycol, capric acid, caproic acid, caprylic acid, caprylic/capric triglyceride, diethylene glycol, diethylene glycol monoethyl ether, glycerin, glyceryl dioleate, glycerol monooleate, glycerol trioleate, hexylene glycol, isopropylmyristate, isopropylpalmitate, linoleic acid, methyl laurate, oleic acid, oleyl alcohol, polyethylene glycol 200, polyethylene glycol dilaurate, propyl oleate, propylene glycol, squalene, and the like.

Figure 2D:
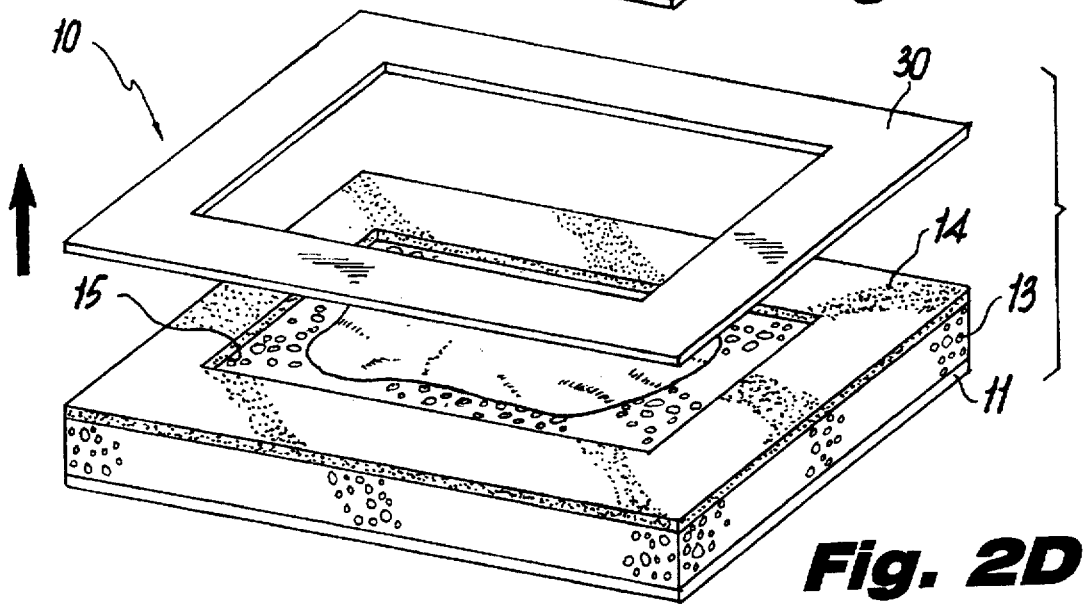
Figure 2E:
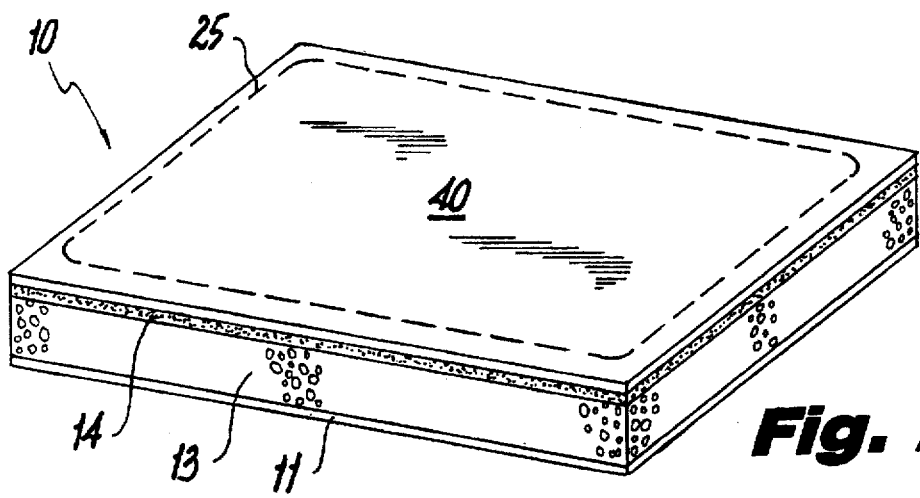

In FIG. 2D, temporary release liner 30 is removed leaving adhesive 14 to remain incorporated in zone 15 of foam layer 13. Then, as shown in FIG. 2E, second, or final, release liner 40 is applied to lower surface 16 of the foam layer where it remains until such time as drug delivery device 10 is to be applied. If desired, drug delivery device 10 can be trimmed, e.g., along line 25.

Drug delivery device 10 can also be fabricated by applying adhesive directly to the adhesive zone of the lower surface of the foam layer in the barrier layer/foam layer composite and, following the evaporation of any solvent with which the adhesive may be formulated, applying the drug composition to the drug depot zone of the foam layer. This procedure lends itself to a continuous or semicontinuous manufacturing operation, e.g., feeding the barrier layer/foam layer composite in the form of a continuous or lengthy strip to an adhesive coating head where the adhesive is applied, passing the coated strip through an oven to accelerate evaporation of the solvent present in the adhesive, incorporating the drug into the drug depot zone, applying a final release liner and cutting the strip into individual drug delivery device units of desired length.

Figure 3:
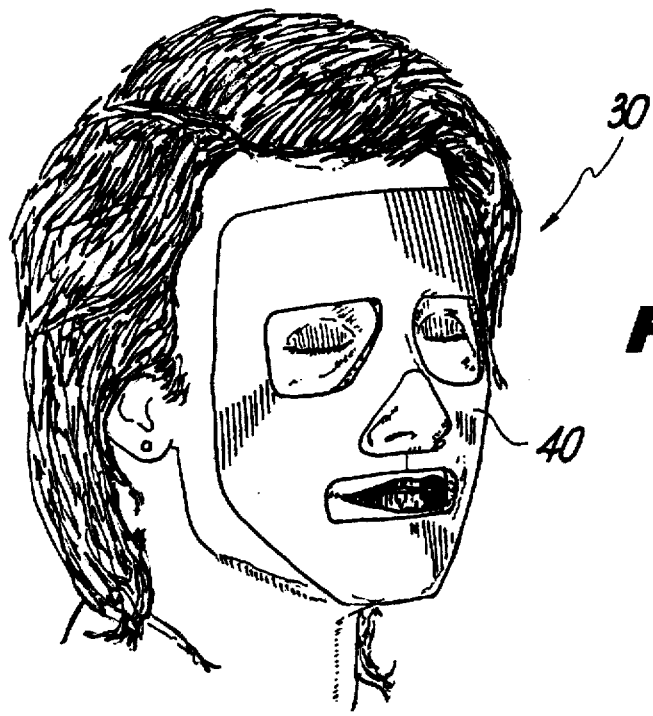
FIGS. 3 and 3A illustrate the from and reverse sides of another embodiment of a drug delivery device herein provided as a facial mask for delivering one or more dermatologically and/or cosmetically beneficial active agents to facial skin; and, FIG. 4 illustrates another type of facial mask assembled in situ from several units of the drug delivery device of this invention each having its own configuration.
Figure 3A:
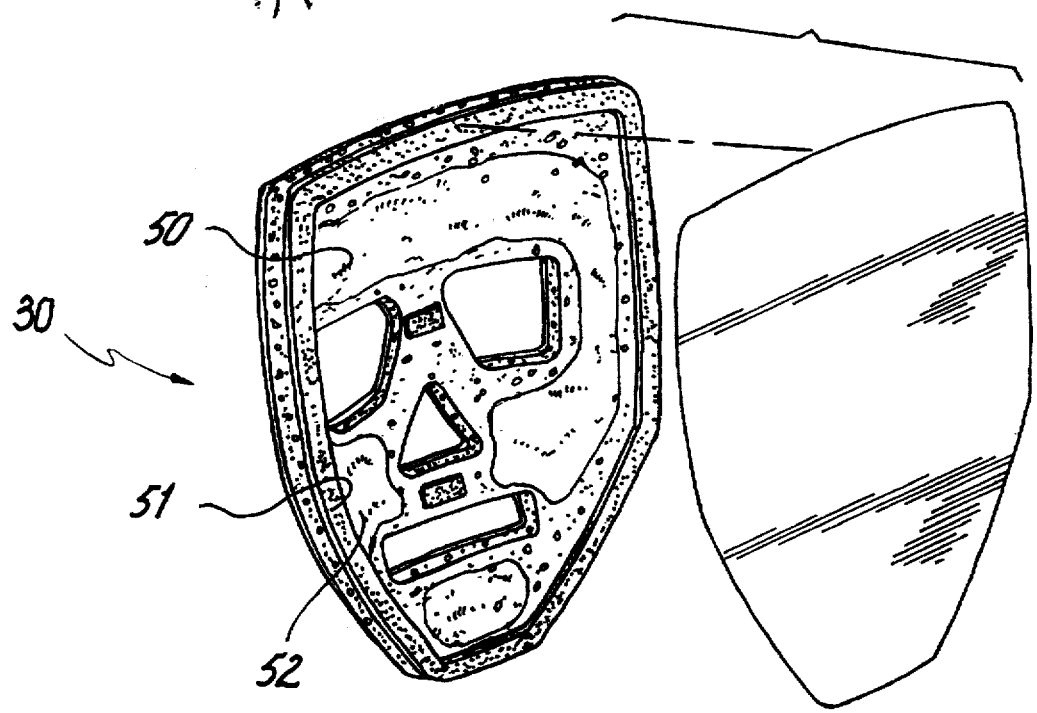

Drug delivery device 10 can be manufactured in a variety of sizes and shapes and can be planar or three-dimensional. FIGS. 3 and 3A illustrate front and reverse views 40 and 50, respectively, of single piece facial mask 30 constructed in accordance with the present invention. Mask 30 can either be manufactured as an entirely planar unit or it can be formed, e.g., by vacuum molding or casting, into a unit shaped to fit the contours of the face. Contact adhesive 51 can be applied not only to an adhesive zone defined along the perimeter of the mask but to one or more additional locations to promote a more secure attachment of the mask to the face. Drug depot zone 52 can be filled with any one of several known and conventional drug compositions for treating dermatological disorders or improving cosmetic conditions such as dry skin, ache, keratoses, psoriasis, eczema, pruritus, age spots, lentigines, melasmas, wrinkles, warts, blemishes, hyperpigmentation, inflammatory dermatoses, skin changes associated with aging, etc.

Figure 4:
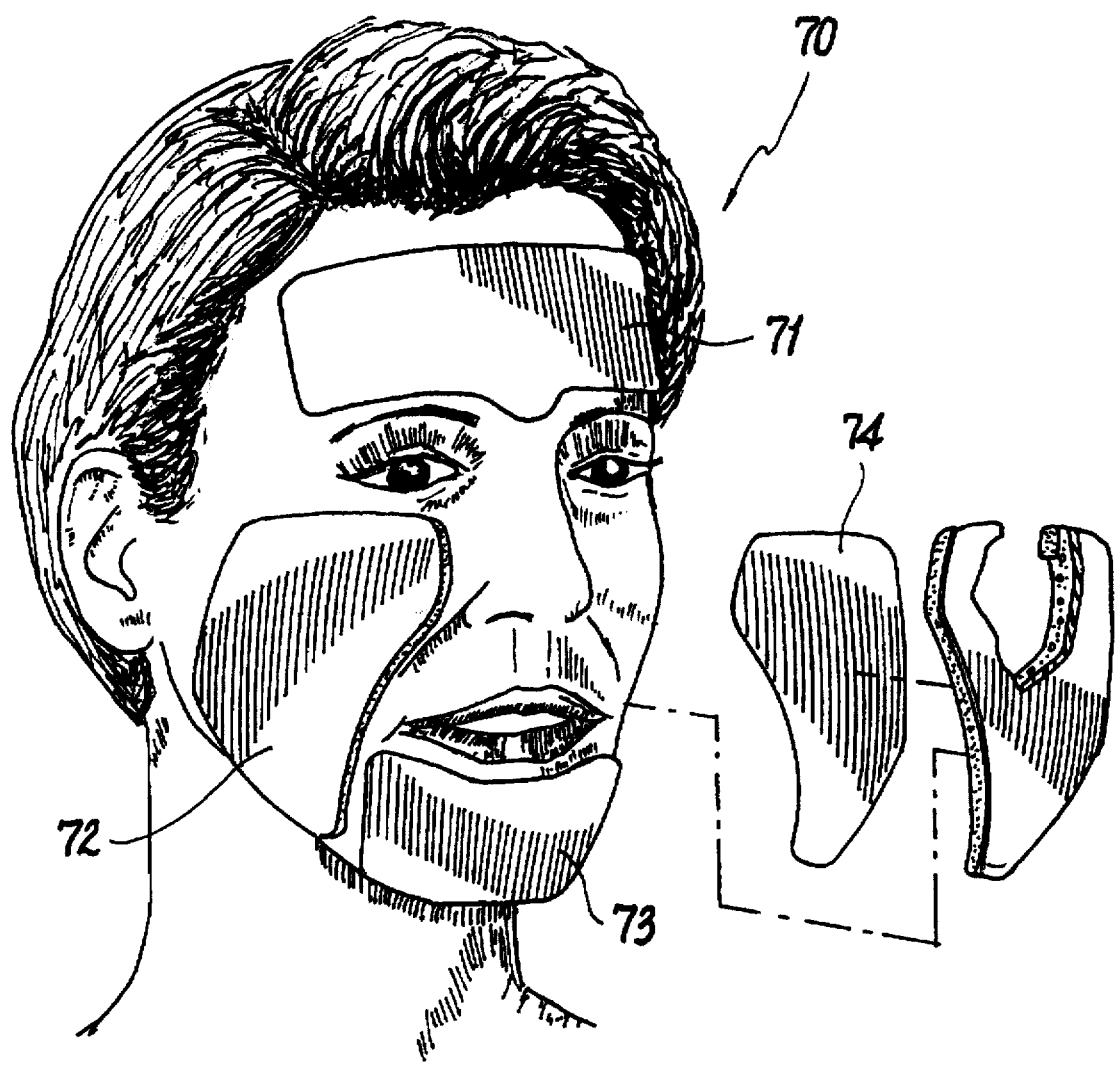

FIG. 4 illustrates in front view another type of facial mask 70 made up of several elements 71–74 each possessing, as shown in the cut-away view of element 74, the construction of drug delivery device 10. Elements 71–74 can be separated from each other (as shown) or they can be made to slightly overlap to provide more complete coverage. As in the case of facial mask 30 of FIG. 3, mask 70 can contain one or more dermatologically or cosmetically active agents for the treatment of facial skin.

The following examples illustrate drug delivery devices within, and for comparison purposes, outside the scope of the invention.

EXAMPLES 1–3

Comparative Examples 1–3

These examples illustrate the effects of using adhesives and nonadhesive bonding on the MVTRs of the barrier film components of several drug delivery devices. The results are shown in Table 1.

TABLE 1

Effects of Bonding Technique on MVTR

| | Barrier Layer[1] (mils) | Bonding/Lamination Technique | MVTR of Barrier Layer | MVTR of Barrier Layer & Foam Layer Composite | Percent Reduction (Increase) in MVTR |
|---|---|---|---|---|---|
| Control | 1.5 | None | 1080 | — | — |
| Comp. Ex. 1 | 1.5 | Polyacrylic Adhesive[2], 1 mil | 690 | — | 36 |
| Comp. Ex. 2 | 1.5 | Polyacrylic Adhesive[2], 3 mils | 470 | — | 55 |
| Comp. Ex. 3 | 1.5 | Adhesive[3], <1 mil | 810 | — | 25 |
| Ex. 1 | 1.0 | Flame | 1375 | 1130 | 18 |
| Ex. 2 | 1.5 | Flame | 1080 | 1255 | (16 increase) |
| Ex. 3 | 1.5 | Vacuum Lamination | 1100 | 1075 | 2 |

[1]Polyurethane film.
[2]Gelva ® (Monsanto Inc.).
[3]Tycel ® (Lord Corp. Industrial Coating Div., Erie, PA).

These data show that the use of adhesives resulted in relatively large reductions in the MVTR of the uncoated barrier layer film. Thus, each of three separate applications of adhesive (Comparative Examples 1–3) reduced the MVTR of the control barrier layer by 36, 55 and 25 percent, respectively. The use of flame bonding and vacuum lamination, in contrast, had considerably less adverse effect on MVTR and in the barrier layer/foam layer composite of Example 2, actually provided a 16% increase in MVTR.

EXAMPLE 4

Comparative Examples 4 and 5

These examples illustrate the relationship of the strength of the bond between the barrier layer and the foam layer and peel strength. The results are set forth in Table 2.

TABLE 2

Relationship of Barrier Layer-Foam Layer Bond Strength and Peel Strength

| | Bond Strength Between Barrier/ Foam Layer Composite, N | Peel Strength (from Stainless Steel), N | Percent By Which Peel Strength Is Less Than Bond Strength | Extent of Delamination |
|---|---|---|---|---|
| Comp. Ex. 4[1] | 4.1 | 4.1 | 0 | Foam layer entirely delaminated |
| Comp. Ex. 5[2] | 3.7 | 2.6 | 30 | Foam layer partially delaminated |
| Ex. 4[2] | 5.6 | 2.9 | 48 | Foam layer remained completely bonded to the barrier layer |

[1]Nonreticulated polyurethane foam, 2 lb/ft³, on 1.5 mil polyurethane barrier film, with 1 mil contact adhesive.
[2]Reticulated polyurethane foam, 4 lb/ft³, on 1.5 mil polyurethane barrier film with 1 mil contact adhesive.

As these data show, for the particular drug delivery devices tested the peel strength needed to be nearly half that of the bond strength for the foam layer to remain completely bonded to the barrier layer.

What is claimed is:

1. A process for manufacturing a nonocclusive drug delivery device which comprises:

a) bonding a substantially moisture vapor permeable, liquid impermeable, flexible thermoplastic barrier layer to the upper surface of an open cell, flexible, oleophilic thermoplastic foam layer possessing predetermined adhesive and drug depot zones;

b) applying a first release liner possessing an opening and having a layer of contact adhesive upon its lower surface to the lower surface of the foam layer with the adhesive contacting and infiltrating the adhesive zone of the foam layer the opening in the release liner exposing a portion of the lower surface of the foam layer including the drug depot zone;

c) introducing a predetermined quantity of drug composition comprising a drug and an oleophilic drug delivery vehicle into the exposed drug depot zone;

d) removing the first release liner to expose the entire lower surface of the foam layer, the contact adhesive remaining within the adhesive zone of the foam layer; and, e) applying a second release liner to the lower surface of the foam layer to fully seal said surface.

2. The process of claim 1 wherein the barrier layer is nonadhesively bonded to the foam layer.

3. The process of claim 2 wherein the barrier layer is flame bonded or vacuum bonded to the foam layer.

4. The process of claim 1 wherein in step (a) the adhesive zone is separated from the drug depot zone by a predetermined drug migration barrier zone and in step (b) the release liner additionally exposes the drug migration barrier zone.

* * * * *